United States Patent

Vom Berg et al.

[11] Patent Number: 6,093,145
[45] Date of Patent: Jul. 25, 2000

[54] BRAIN SPATULA

[75] Inventors: Ingo Vom Berg, Trossingen; Gebhard Herrmann, Irndorf; Dieter Weisshaupt, Immendingen; Paul Wieneke, Rietheim-Weilheim, all of Germany

[73] Assignee: Aesculap AG & Co. KG, Tuttlingen, Germany

[21] Appl. No.: 09/366,969

[22] Filed: Aug. 4, 1999

Related U.S. Application Data

[63] Continuation of application No. PCT/EP98/00514, Jan. 31, 1998.

[30] Foreign Application Priority Data

Feb. 10, 1997 [DE] Germany .................. 197 04 997

[51] Int. Cl.[7] .................................................. A61B 17/02
[52] U.S. Cl. .................... 600/206; 600/210; 600/235
[58] Field of Search .................................. 600/206, 210, 600/235, 201

[56] References Cited

U.S. PATENT DOCUMENTS

| | | |
|---|---|---|
| 1,944,009 | 1/1934 | Homer . |
| 3,288,131 | 11/1966 | Garland . |
| 3,522,800 | 8/1970 | Lesser ....................................... 600/206 |
| 3,882,855 | 5/1975 | Schulte et al. . |
| 4,048,987 | 9/1977 | Hurson ..................................... 600/206 |
| 4,263,900 | 4/1981 | Nicholson . |
| 4,421,107 | 12/1983 | Estes et al. .............................. 600/206 |
| 4,945,896 | 8/1990 | Gade . |

FOREIGN PATENT DOCUMENTS

| | | |
|---|---|---|
| 0 143 124 | 6/1985 | European Pat. Off. . |
| 80 17 520 | 9/1980 | Germany . |
| 215 468 A1 | 11/1984 | Germany . |

OTHER PUBLICATIONS

Portnoy, Harold D. and Croissant, Paul D., "A Padded Brain Retractor", *Surgical Neurology*, vol. 1, No. 4, Jul. 1973, p. 243.

*Primary Examiner*—Jeffrey A. Smith
*Attorney, Agent, or Firm*—Barry R. Lipsitz; Ralph F. Hoppin

[57] ABSTRACT

In order to achieve as uniform a distribution of pressure as possible during the application to the brain of a brain spatula with a band-like strip consisting of a pliable and inherently stable material it is suggested that the strip be enveloped by a soft, elastically deformable material which projects laterally beyond the strip at the side edges of the strip and the deformability of which increases from the side edges of the strip towards the edge of the soft material.

15 Claims, 2 Drawing Sheets

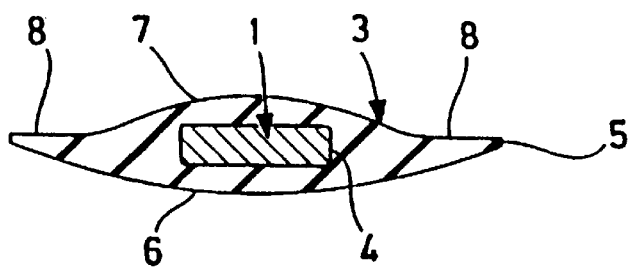
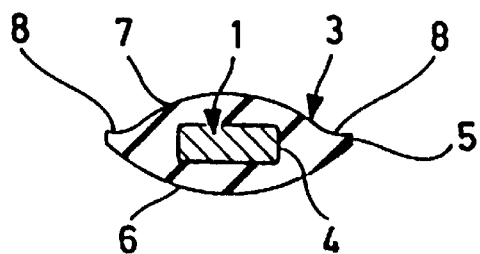
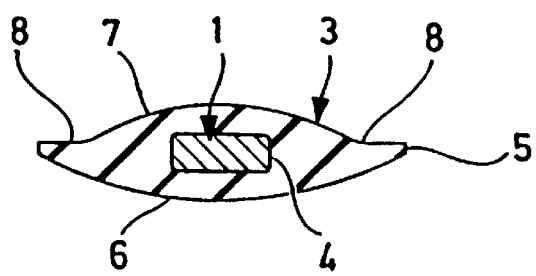
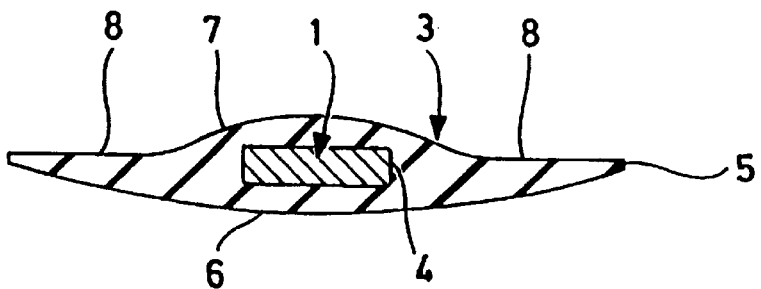
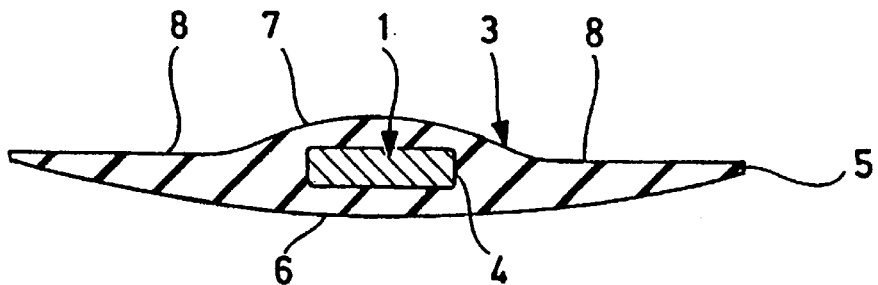

BRAIN SPATULA

This application is a continuation of International Application No. PCT/EP98/00514, filed Jan. 31, 1998, and published as document WO 98/34544.

BACKGROUND OF THE INVENTION

The invention relates to a brain spatula with a band-like strip consisting of a pliable and inherently stable material.

Brain spatulas have been used for a long time in neurosurgery in order to retract the brain parenchyma and thus keep a channel free into the depth of the operating area. The most common structural form is a simple strip of sheet metal consisting of a metal strip which can be bent by hand and the surface of which is already, however, clearly outlined on the brain after a few minutes. Particularly noticeable are the pressure marks of the lateral spatula edges which indicate a high local compression stress. This compression stress can lead to corresponding injuries.

It is known to round off brain spatulas in the area of the edges in order to reduce the compression stress as a result. It is not, however, possible as a result of this measure to avoid injuries to the desired degree.

SUMMARY OF THE INVENTION

Attempts to mitigate the trauma caused by brain spatulas by way of a plastic surface coating have also been unsuccessful.

The object of the invention is to design a generic brain spatula such that high local compression stresses can be avoided.

This object is accomplished in accordance with the invention, in a brain spatula of the type described at the outset, in that the strip is enveloped by a soft, elastically deformable material which projects laterally beyond the strip at the side edges of the strip and the deformability of which increases from the side edges of the strip towards the edge of the soft material.

Such a configuration makes an even pressure distribution of the retraction forces possible and ensures adaptation of the spatula surface to the brain matter without pressure points. Nevertheless, the inherent stability of the spatula can, altogether, be achieved by the strip embedded in the soft material.

It may be provided in accordance with a preferred embodiment for the material thickness of the soft material to decrease from the side edges of the strip towards the edge. This decrease in the material leads to an increase in the deformability and thus to a decrease in the transferable retraction forces from the center of the spatula towards the edge. It is advantageous when the total width of the soft material is at least twice as much as the width of the strip so that apart from the inherently stable strip a sufficiently broad area remains, in which only soft material is provided and in which the deformability gradually increases.

It may, in particular, be provided for the total width of the soft material to be up to five times as great as the width of the strip.

A particularly gentle application results when it is provided in accordance with a preferred embodiment for the cross section of the soft material to be limited in the area of the strip by outwardly curved, arcuate sections. No edges whatsoever then result in the area of the soft material but rather a rounded, outwardly curved contour which embeds the inherently stable strip within it.

The arcuate section can, in particular, extend on one side of the soft material over its entire width so that this results in a constant course free of edges and projections.

On the opposite side it may be provided for the arcuate section to extend only over a central area and to merge on both sides into straight sections extending essentially parallel to the strip. As a result, the material thickness may be reduced in the edge strip located laterally next to the inherently stable strip and so an increased deformability can be achieved towards the edge.

The boundary lines of the cross section of the soft material can, in particular, run together at the edges at an acute angle, for example, at an angle of between 10° and 30°.

The lateral edge strips therefore act like lateral vanes or sealing lips which transfer retraction forces outwards from the strip which become ever smaller, wherein these forces continuously decrease to zero towards the edge due to the acute-angled course.

The soft material can have in the area of the strip a layer thickness which is at least as great as the thickness of the strip. As a result, an adaptation to the contour of the brain, and thus an optimum balance of pressure is also made possible in this area due to an elastic compression of the soft material.

Alternatively or in addition, it may be provided for the Shore hardness of the soft material to decrease from the side edges of the strip towards the edge. This measure also serves to increase the deformability of the soft material from the strip towards the edge.

For example, the Shore hardness may, in the area of the side edges, be between 50 and 70, in the area of the edge between 20 and 40.

The soft material may consist, in particular, of silicone.

In a preferred embodiment, it is provided for the strip to be connected at one end to a handle.

This handle can be of a band-like design and have a width which is greater than the width of the strip. In particular, the width of the handle corresponds essentially to the width of the soft material.

The following description of preferred embodiments of the invention serves to explain the invention in greater detail in conjunction with the drawings.

BRIEF DESCRIPTION OF THE DRAWINGS

FIG. 2: a sectional view along line 2—2 in FIG. 1;

FIG. 3: a view similar to FIG. 2 with a brain spatula having a smaller width;

FIG. 4: a view similar to FIG. 2 with a brain spatula having a narrower strip;

FIG. 5: a view similar to FIG. 2 with a brain spatula having a greater width of the soft material and FIG. 6: a view similar to FIG. 2 with an even greater width of the soft material.

DETAILED DESCRIPTION OF THE INVENTION

Figure 1:
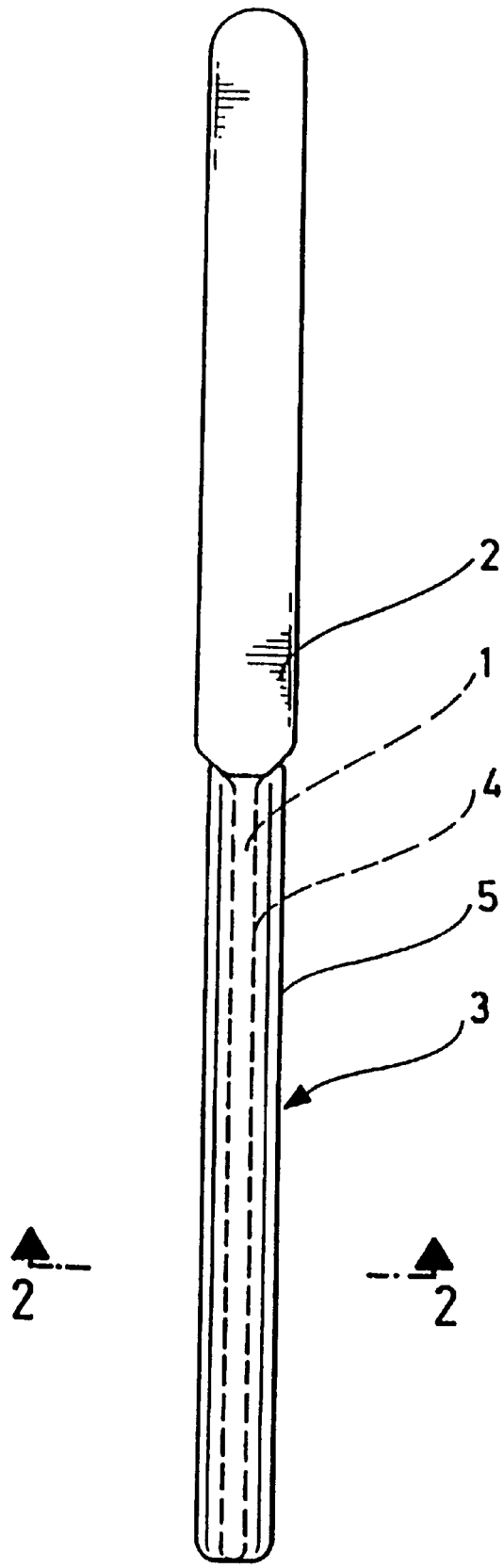
FIG. 1: a plan view of a first preferred embodiment of a brain spatula.

The brain spatula shown in the drawings comprises a narrow, elongated strip 1 consisting of a pliable and inherently stable material, for example, of high-grade steel or of titanium. Inherently stable merely means that this strip retains its shape after bending; it is therefore understood that this material can be bent by hand.

The strip preferably has a rectangular cross section but a different cross-sectional shape could, in principle, also be used.

At one end the strip 1 merges into a broader, band-like handle 2 which can be designed in one piece with the strip 1 but can also be an independent structural part which is connected to the strip 1.

The strip 1 is embedded in a casing 3 consisting of soft material, for example, of silicone. This casing 3 surrounds the strip 1 on all sides; in the area of the upper side and the underside of the strip 1 the casing 3 is configured with a layer thickness which corresponds approximately to the thickness of the strip 1. Beginning at the side edges 4 of the strip 1, the casing 3 continues laterally as far as its edge 5 over a width which corresponds at least to half the width of the strip 1 but which can be substantially larger; for example, the casing 3 can, altogether, be five times as broad as the strip 1.

The casing 3 is limited on one side by an arcuate, outwardly curved boundary line 6, which extends over the entire width of the casing 3, on the opposite side by an arcuate boundary line 7 which is curved in the opposite direction but is curved outwards only in the region of the strip 1 and in the bordering areas adjoining thereto on both sides whereas, in the edge areas located further outwards, it merges into straight sections 8 which extend parallel to the strip 1 as far as the edge 5. The transition between the curved boundary line 7 and the straight sections 8 is not in the form of steps but smooth.

In the region of the edge 5, the boundary line 6 and the sections 8 run together at an acute angle; the angle may be between 10° and 30°. The width of the strip 1 and the width of the casing 3 may be selected to be different; in the embodiments of FIGS. 2 to 6, different dimensioning possibilities are illustrated.

It is common to all the embodiments that the material thickness of the casing 3 decreases from the side edges 4 towards the edge 5 so that, as a result, an increased deformability is achieved in the direction towards the edge 5. This increased deformability also means that the transferable retraction forces decrease from the strip 1 towards the edge 5 so that, altogether, a uniform introduction of pressure to the adjoining brain is achieved.

The increased deformability is achieved in the embodiments described thus far merely due to the fact that the material thickness of the casing 3 decreases towards the edge 5.

Alternatively, it could also be provided for the Shore hardness of the material of the casing 3 to decrease from the center towards the edge 5. This could take place with a constant thickness of the casing 3 but it would be particularly advantageous when this measure is combined with a decrease in the material thickness towards the edge 5. For example, a material could be used which has Shore hardnesses of between 50 and 70 in the region of the side edges but Shore hardnesses of between 20 and 40 in the region of the edge 5.

What is claimed is:

1. A brain spatula, comprising:

band-like strip with side edges;

said strip comprising a pliable and inherently stable material, and a soft, elastically deformable material enveloping said strip and projecting laterally beyond the strip at the side edges of the strip; wherein:

a material thickness of said soft material decreases from the sides edges of the strip towards respective edges of the soft material such that its deformability increases from the side edges of the strip towards the respective edges of the soft material;

a cross section of the soft material is limited in an area of the strip by first and second outwardly curved arcuate sections;

the first arcuate section extends on one side of the soft material over its entire width;

the second arcuate section extends on an opposite side of the soft material only over a central area; and both sides of the second arcuate section merge into straight sections that extend essentially parallel to the strip.

2. The brain spatula of claim 1, wherein;

the total width of the soft material is at least twice as much as the width of the strip.

3. The brain spatula of claim 2, wherein:

the strip comprises titanium.

4. The brain spatula of claim 1, wherein:

the total width of the soft material is up to five times as great as the width of the strip.

5. The brain spatula of claim 1, wherein:

boundary lines of the cross section of the soft material run together at the edges of the soft material at an acute angle.

6. The brain spatula of claim 5, wherein:

the acute angle is between 10° and 30°.

7. The brain spatula of claim 1, wherein:

the soft material has, in the area of the strip, a layer thickness at least as great as a thickness of the strip.

8. The brain spatula of claim 1, wherein:

a Shore hardness of the soft material decreases from the side edges of the strip towards the edges of the soft material.

9. The brain spatula of claim 8, wherein:

the Shore hardness in the area of the side edges of the strip is between 50° and 70°.

10. The brain spatula of claim 8, wherein:

the Shore hardness in the area of the edges of the soft material is between 20 and 40.

11. The brain spatula of claim 1, wherein:

the soft material comprises silicone.

12. The brain spatula of claim 1, further comprising:

a handle connected to one end of the strip.

13. The brain spatula of claim 12, wherein:

the handle is of a band-like design and has a width greater than the width of the strip.

14. The brain spatula of claim 13, wherein:

the width of the handle corresponds essentially to the width of the soft material.

15. The brain spatula of claim 1, wherein:

the strip comprises titanium.

* * * * *